Figure 1:
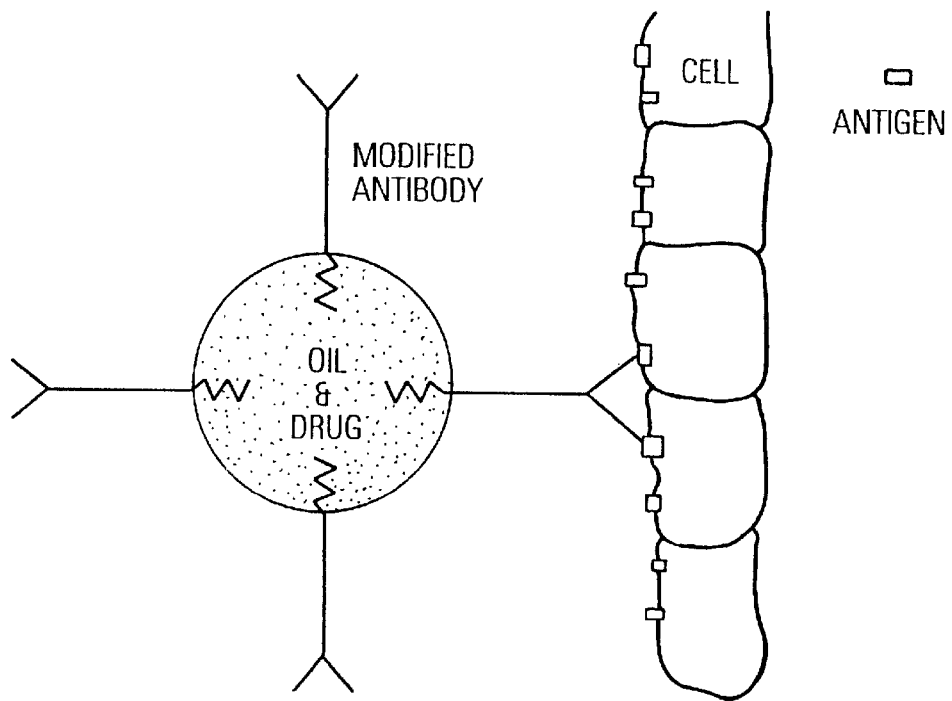
Figure 2:
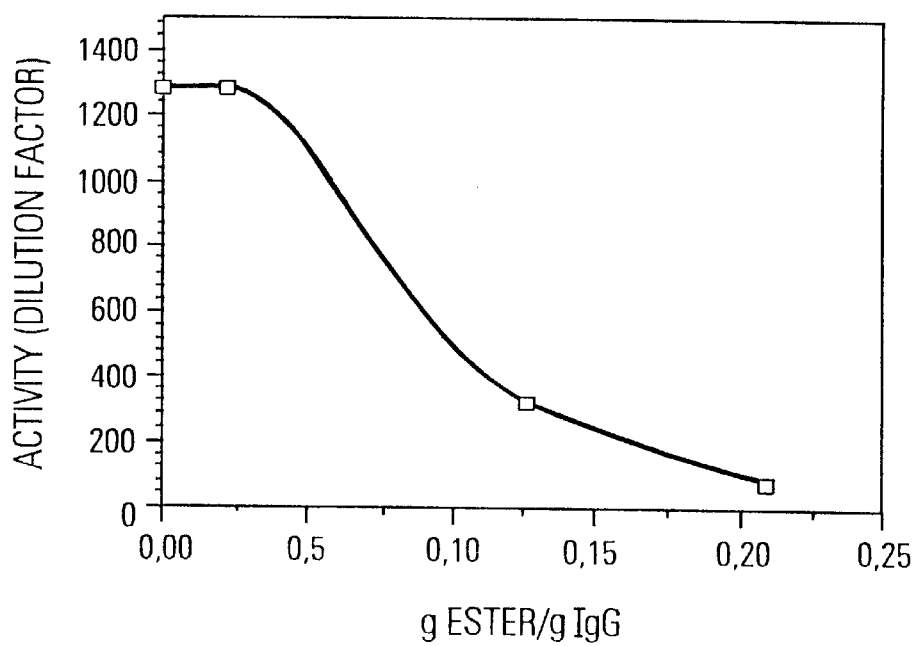
Figure 3:
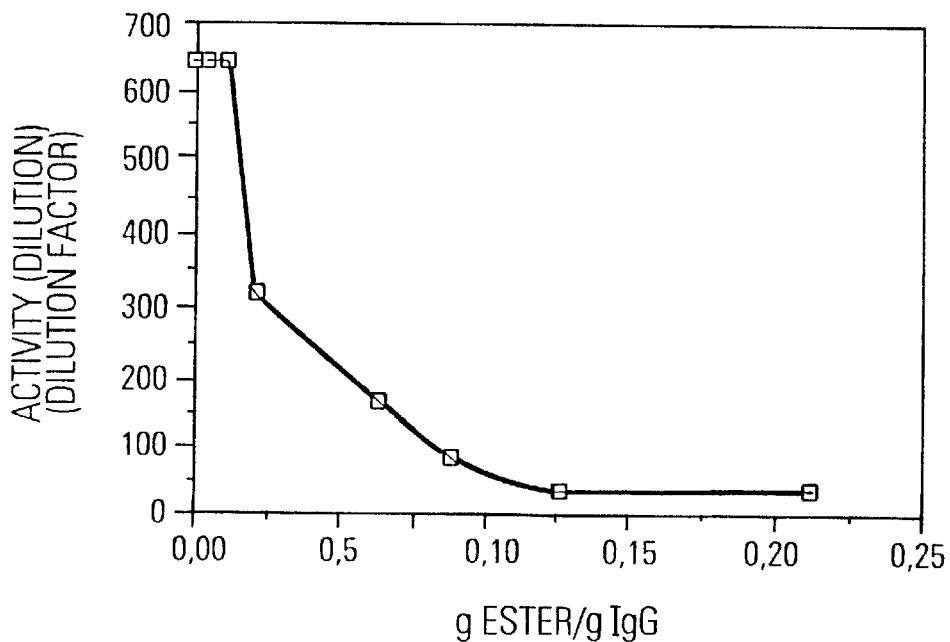
Figure 4:
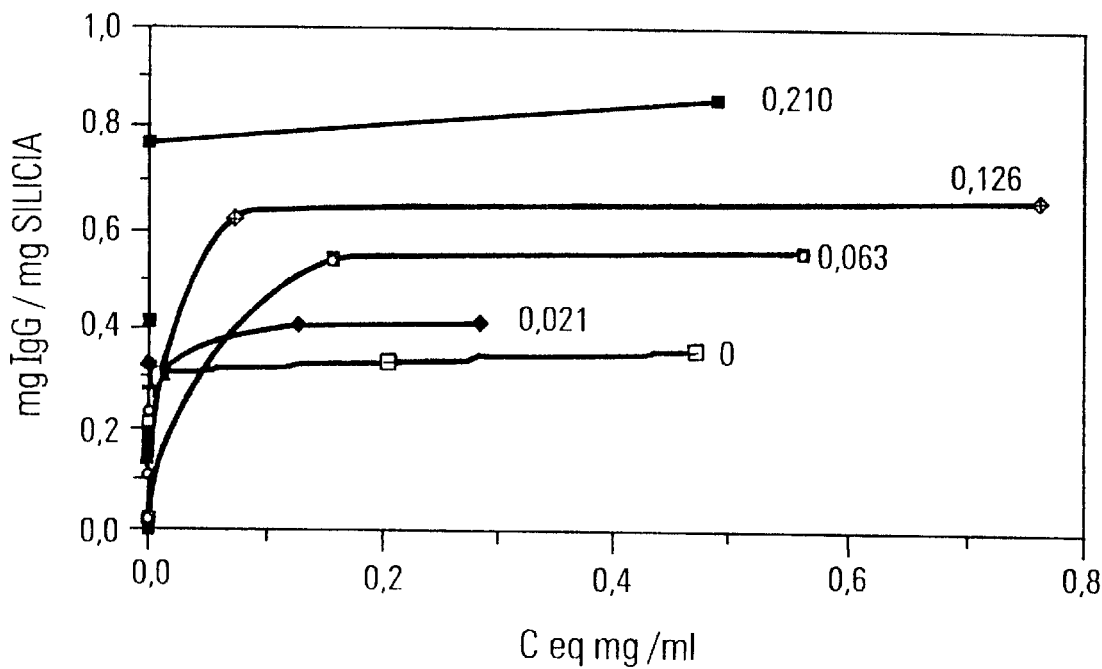
Figure 5:
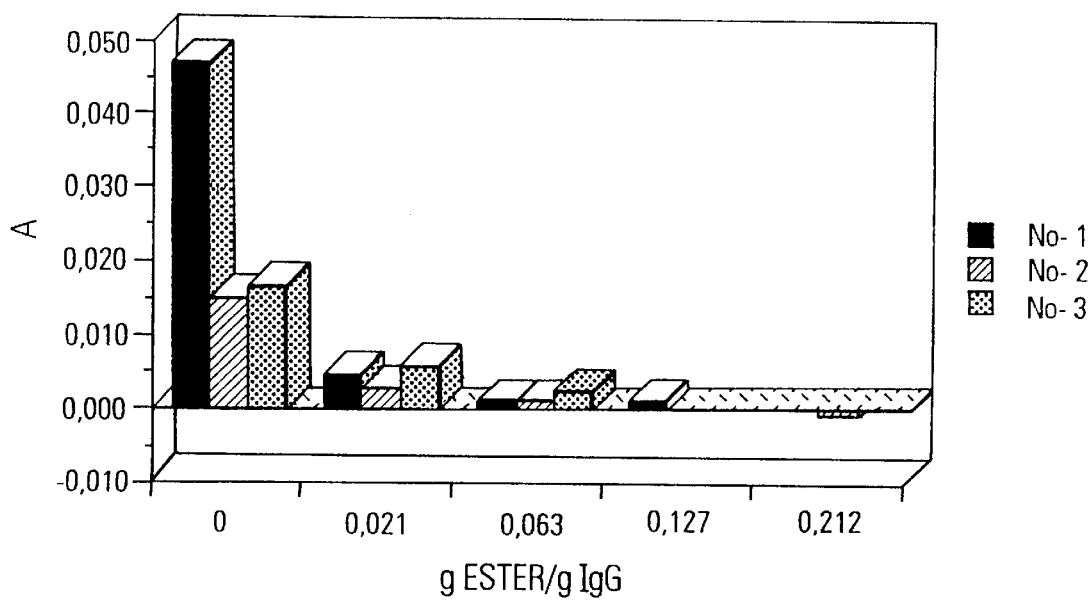
Figure 6:
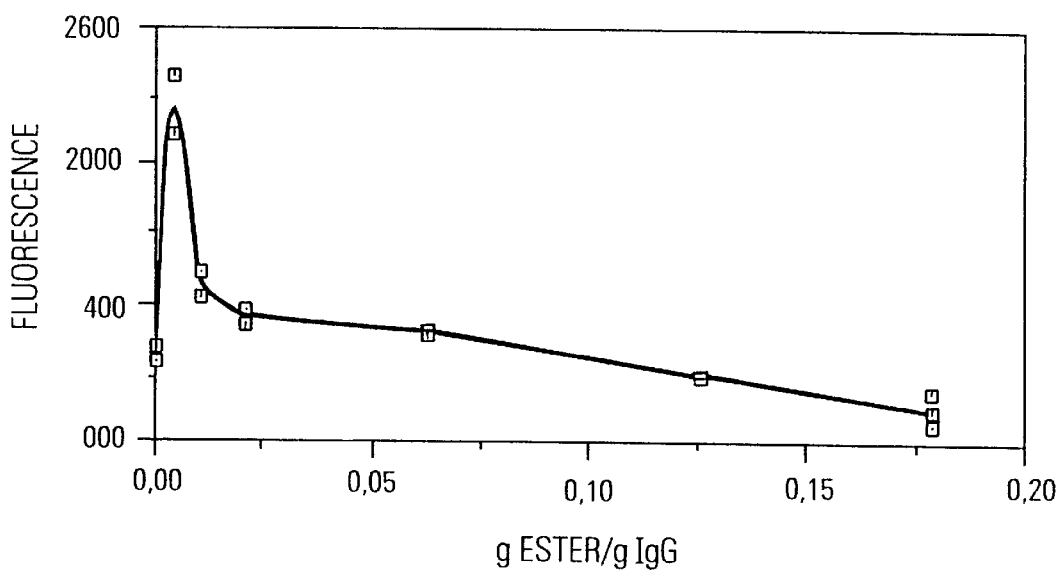

United States Patent [19]
Magdassi et al.

[11] Patent Number: 5,858,382
[45] Date of Patent: Jan. 12, 1999

[54] METHOD AND PHARMACEUTICAL COMPOSITIONS FOR DRUG TARGETING

[75] Inventors: Shlomo Magdassi; Zichria Zakay Rones, both of Jerusalem; Moshe Linevitz, Ramat Gan; Oren Shanberg, Bnei Brak, all of Israel

[73] Assignee: Yissum, Research Development Company of the Hebrew University of Jerusalem, Jerusalem

[21] Appl. No.: 592,432

[22] PCT Filed: Aug. 3, 1994

[86] PCT No.: PCT/EP94/02577

§ 371 Date: Jul. 8, 1996

§ 102(e) Date: Jul. 8, 1996

[87] PCT Pub. No.: WO95/03829

PCT Pub. Date: Feb. 9, 1995

[30] Foreign Application Priority Data

Aug. 3, 1993 [IL] Israel ............................... 106578

[51] Int. Cl.$^6$ ................................. A01N 25/00
[52] U.S. Cl. .................. 424/405; 424/406; 424/450; 424/489; 424/490; 424/498; 424/502; 514/938
[58] Field of Search ................... 424/450, 489, 424/490, 498, 502, 405, 406; 514/938

[56] References Cited

U.S. PATENT DOCUMENTS 4,634,681  1/1987  Giaever et al. .................. 436/518
5,576,016  11/1996  Amselem et al. .................. 424/450

FOREIGN PATENT DOCUMENTS 0331755  9/1989  European Pat. Off. .
0391369  10/1990  European Pat. Off. .

OTHER PUBLICATIONS

Davis et al, Drugs Exptl. Clin. Res., XI(9), pp. 633–640 (1985).
Database WPI, Week 8807, Derwent Pub. Ltd. AN 88–045802 & JP–A–63–002923.
Database WPI, Week 8848, Derwent Pub. Ltd. AN 88–341492 & JP–A–63–253021.
Journal of Biological Chemistry, vol. 225, No. 17, Sep. 10, 1980, Huang et al., "Monoclonal Antibody Covalently Coupled . . . ".

Primary Examiner—Neil S. Levy
Attorney, Agent, or Firm—Birch, Stewart, Kolasch & Birch, LLP

[57] ABSTRACT

A pharmaceutical composition comprising an oil/water emulsion wherein the oil droplets contain a drug in dissolved or dispersed or solubilized form. The droplets are further coated with adsorbed native or modified antibodies which provide targeting of the droplets and the drug. The process for preparing this composition comprises the steps of (i) dissolving or dispersing a drug in an oil phase, (ii) preparing an oil/water emulsion, (iii) obtaining surface-active antibodies by chemical or physical attachment of hydrophobic groups to the antibodies, and (iv) mixing the surface-active antibody with the emulsion.

5 Claims, 4 Drawing Sheets

FIG.7

Emulsion droplets attached to HSV infected BSC-1 cells, Gia surface active antibodies.

METHOD AND PHARMACEUTICAL COMPOSITIONS FOR DRUG TARGETING

The present invention relates to pharmaceutical compositions and a method for drug targeting. More specifically said invention relates to pharmaceutical compositions containing an oil/water emulsion wherein a drug is dissolved or solubilized or dispersed inside the oil droplets and wherein said emulsion droplets are coated with adsorbed native and modified antibodies. The invention relates also to a process for the preparation of said pharmaceutical compositions and to a method for drug targeting toward specific molecules or sites in the body, comprising administration to a host an effective amount of above mentioned pharmaceutical compositions.

Emulsion droplets are coated with adsorbed native and/or modified antibodies which are capable of interacting with specific molecules or antigenic determinants. Therefore, the droplets will be directed towards specific molecules or sites in the body. When a drug is dissolved, dispersed or solubilized inside the oil droplet, a novel drug targeting system is obtained.

BACKGROUND OF THE INVENTION

The present invention relates to drug targeting by small emulsion droplets, using biologically active targeting molecules. The advantages of being able to direct the drug to the tissue or cells where it is required, and to minimize the amount delivered to inappropriate sites has implications for many clinical situations, such as cancer chemotherapy, inflammations and viral infections (Davis S. S et al. Drug Exptl. Clin. Res. 9, 632, 1985).

In the past, several attempts to achieve drug targeting were reported, by using polyclonal and monoclonal antibodies. These attempts include:

1. Direct chemical attachment of drug molecules to an antibody molecule.
2. Chemical attachment of drugs to antibodies through the use of a linkage polymer molecule such as dextran.
3. Attachment of small antibodies to small biodegradable polymeric particles, by covalent linkage by direct adsorption or by adsorption via protein A.
4. Coupling of liposomes with monoclonal antibodies via hydrophobic modification of the antibody.

The above suggested method to achieve drug targeting have many disadvantages:

a) Covalent attachment of drug molecules require development of a chemical binding process for each drug to be tested.
b) Direct attachment to the antibody may reduce its biological activity.
c) only a limited amount of drug molecules may be bound.
d) The clinical effects of the drugs may be altered upon chemical attachment.
e) Possible leakage of drugs if liposomes are used.
f) Desorption of the antibodies may occur if it is physically adsorbed to a solid particle.

The present invention will provide a novel drug targeting method, which would overcome most of the above disadvantages, by the use of emulsions and micro emulsions.

BRIEF DESCRIPTION OF THE INVENTION

The present invention relates to pharmaceutical compositions containing an oil/water emulsion wherein a drug is dissolved or dispersed or solubilized inside the oil droplets and wherein said emulsion droplets are coated with adsorbed native and/or modified antibodies.

The present invention further relates to a process for the preparation of said pharmaceutical compositions comprising:

a) dissolving the desired drug in an oil phase;
b) formation of an oil/water emulsion;
c) formation of a surface-active-antibody by chemical attachment of various hydrophobic groups to the antibodies;
d) mixing the surface-active antibody with the emulsion.

The present invention also relates to a method for drug targeting towards specific molecules or sites in the body (such as antigenic determinants), comprising administration to a host of an effective amount of pharmaceutical composition according to claim 1.

DESCRIPTION OF THE INVENTION

The invention is based on a simple process, which may be applied to various types of drugs.

As described in FIG. 1, the final composition contains oil emulsion droplets onto which native or chemically modified antibodies are adsorbed. A hydrophobic drug is dissolved or solubilized inside the oil droplet, and there-fore, the drug may be targeted to specific sites by the antibodies. The following principle steps are required for obtaining the final composition:

1. Chemical attachment of various hydrophobic groups to the antibodies. This step will lead to formation of a "surface-active-antibody".
2. Formation of an O/W emulsion by various simple methods which are well established. The oil phase initially contains the desired drugs.
3. Mixing the "surface-active-antibody" with the emulsion, for a short period of time. The resulting composition is demonstrated in FIG. 1.

This process is very simple and may be applied rapidly to various types of drugs, antibodies, and emulsions. The main advantages of the proposed method are:

1. The process is very versatile and is based on a modular approach, which may be adopted by the final user, provided the drug has a suitable solubility in the emulsion droplets, or may be dispersed or solubilized in the oil phase.
2. It is possible to use various types of oils for preparation of the emulsion to meet the requirement of drug solubility or dispersion.
3. The drug molecules are not subjected to any chemical modification; the original drug is maintained through the whole process.
4. Due to its hydrophobicity, the drug will not leak significantly from the oil droplets upon storage.
5. Desorption of the antibodies is a very unlikely event since the antibody has become a "surface-active-antibody" with improved adsorption capability; more protein molecules are adsorbed more strongly to the oil-water interface, than the native antibody.
6. The chemical modification of the antibodies is very simple and is performed in such a way that the biological activity and antigen recognition is not affected.
7. The same process may be applied to other biologically active substances which have a recognition capability.
8. The same process may be applied even without modification of the antibody by the use of specific molecules such as protein A.

9. The same process may be applied by physical attachment of hydrophobic groups to the antibody without covalent bonding.

10. The emulsion droplets serve as large reservoirs for drugs, and by the antibodies it is possible to obtain high local drug concentration without side effects.

Manner and Process of Making the Invented Composition

The apparatus and materials disclosed herein are merely exemplary, and after understanding the method, other embodiments may be devised.

Step I: Emulsion Preparation

1. The desired drug is dissolved or dispersed in the oil phase, which might be soybean oil, medium chain triglycerides (MCT) or any other oil, with increased or decreased polarity and hydrophobicity. The oil may contain additions such as solubilizers, dispersants, etc.

2. An emulsifier (such as lecithin and pluronic F-68, or a combination of emulsifiers) is dissolved in an aqueous phase.

3. The oil phase is dropwise added to the aqueous phase while stirred by a mechanical or magnetic stirrer.

4. The crude emulsion is further homogenized until the desired droplet size is achieved. This step may be carried out by various instruments, such as polytron (Brinkman Instruments), ultra-torex (Jumble & Kundel), high pressure piston homogenizers, microfluidizer, etc. The whole process for preparation of the emulsion may take less than half an hour. Typical composition contains about 20% W/W oil phase, 1–5% emulsifiers and water or saline up to 100%.

Step II: Antibody Modification

The desired antibody (monoclonal or polyclonal) is coupled to a hydrophobic tail by a simple chemical reaction. During this step some parameters may vary such as the ratio of hydrophobic tails to antibody molecules and the length of the hydrophobic tail. It is important to note that only a slight modification is needed to impose surface activity without decreasing the biological activity.

The process described here is based on the use of active esters of fatty acids, but other methods may also be applied, and also physical adsorption of various groups.

The principle steps are:

1. Formation of N-alkanoyl succinimide ester (active ester) by reacting a fatty acid (chain lengths C8–C18) with N-hydroxy succinimide, as described by Lapidot et al. [J. Lipid Research, 8, 142 (1967)].

2. Mixing the active ester with a solution of the desired antibodies, and formation of alkanoyl antibody, as described by Huang et al. [J. Biological Chem., 235, 8015–8018 (1980)].

3. Purification of the modified antibody by dialysis and/or Sephadex column.

The whole process is simple and requires no special equipment. The reaction conditions are chosen in such a way that the biological activity will not be affected, as will be described in the examples.

Step III: Antibody-Emulsion Interaction

Since the modified antibodies are very surface active, all is needed for their adsorption onto emulsion droplet is simple mixing for about one hour.

The modified antibody solution may be mixed with various volumes of the emulsion. (In some cases it is also possible to mix native and modified antibodies before the adsorption take place.)

After the adsorption process is completed, the final composition is achieved. This composition contains strongly attached antibodies at the oil-water interface and is capable of recognizing specific sites such as virally infected cells or cancer cells, depending on the type of antibody used.

EXAMPLES

1. Modification of IgG with N-caproyl ester was conducted at various ester/IgG ratios. The resulting antibodies were surface-active, having various numbers of attached hydrophobic groups.

After modification was completed, the biological activity was analyzed by quantitative evaluation of the active antibodies against Herpes Simplex Virus by two methods:

Elisa, and fluorescence antibody assay labeling virally infected cells. From the results presented in FIG. 2 it is clear that up to a molar ratio of 4:1, the recognition activity is not affected. The same results are obtained from the recognition of virally infected BSC-1 cells, as presented in FIG. 3. Similar results were obtained for infected Daudi cells (from human origin).

2. A series of modified and native antibodies were adsorbed onto hydrophobic silica particles in order to evaluate the increase in the surface activity. As shown in FIG. 4, the amount of adsorbed antibody increases with the increase of the ratio ether/antibody.

3. The hydrophobic particles, which have adsorbed antibodies, were subjected to several washings with Phosphate Buffer Saline (PBS) in order to evaluate their desorption. As shown in FIG. 5, the native antibody is readily desorbed while almost no desorption was detected for the modified antibodies.

4. A series of native and modified IgG were adsorbed on O/W water emulsions, and their effective activity was evaluated. Emulsion compositions was: 10% W/W soybean oil, 2% W/O lipoid PC and 88% W/W phosphate buffer saline. The adsorption process is based on mixing 1 ml emulsion with 7.3 mg antibody and PBS up to a final volume of 19 ml. The ingredients were gently mixed for 12 hrs at 37° C. The detection of activity was achieved by addition of FITC labeled anti IgG (H+C), mixing and reading the fluorescence after adsorption. It is clear that if the modified IgG will lose its activity, no fluorescence will be detected on the emulsion droplets. The results obtained by a computerized fluorescence microscope indicated, as shown in FIG. 6, that enhancement of activity is indeed obtained with IgG which was modified at a low ester/antibody ratio.

5. The attachment of the antibody may be achieved by adsorption of protein A to the emulsion droplet. This could lead to selective adsorption of the antibody with its Fab fragments facing the external aqueous phase. The new system: emulsion-protein A(native or modified)-antibody is a unique modular and versatile system in which no preparations are needed for each drug-antibody combination.

6. The purpose of the following example is to demonstrate the targeting of emulsion droplets to specific cells by in-vitro experiments.

An oil-in-water emulsion containing an oil soluble fluorescent marker was prepared. Onto this emulsion a modified antibody was adsorbed. (The antibody was modified by attachment of $C_8$. residues of fatty acid, 10% of the total available amine groups.)

The emulsion which contained the adsorbed antibody was added to two plates (30 minutes) which were covered by either normal BSC-1 cells, or BSC-1 cells which were previously infected by Herpes virus (HSV-1). After rinsing the plates it was found by a fluorescence microscope and also by ordinary microscope that emulsion droplets (coated with antibodies) were found only on the infected cells, as presented in FIG. 7.

As a control, a similar experiment was conducted, but without adsorbed antibodies. After rinsing the plates, emulsion droplets were not detected at all.

This example shows that the emulsion droplets having adsorbed antibodies against Herpes virus could be attached specifically onto Herpes infected cells.

We claim:

1. A pharmaceutical composition comprising an oil-in-water emulsion wherein the oil emulsion droplet contains dissolved or dispersed or solubilized a hydrophobic drug and on its surface absorbed antibodies which are modified by attaching hydrphobic groups wherein said composition is made by a process comprising the following steps:
   a) solubilizing, dissolving or dispersing the desired drug in an oil;
   b) forming an oil-in-water emulsion the oil being present in an amount to form oil droplets that contain the desired drug;
   c) forming separately a surface-active-antibody by chemical or physical attachment of various hydrophobic groups to the antibodies; and
   d) mixing the surface-active antibody with the oil-in-water emulsion that contains the desired drug in the oil.

2. The pharmaceutical composition according to claim 1 wherein the oil is of soybean oil, triglycerides, or any other oil with hydrophobic molecules.

3. The pharmaceutical composition according to claim 1 wherein the drug is hydrophobic.

4. The pharmaceutical composition according to claim 1 wherein the drug is useful for cancer chemotherapy, inflammations, and infectious diseases including fungi and viral infections.

5. A process for preparing a pharmaceutical composition which comprises an oil-in-water emulsion wherein the oil emulsion droplet contains dissolved or dispersed or solubilized a hydrophobic drug and on its surface adsorbed antibodies which are modified by attaching hydrophobic groups which comprises:
   a) solubilizing, dissolving or dispersing the desired drug in an oil;
   b) forming an oil-in-water emulsion the oil being present in a amount to form oil droplets that contain the desired drug;
   c) forming separately a surface-active-antibody by chemical or physical attachment of various hydrophobic groups to the antibodies; and
   d) mixing the surface-active antibody with the oil-in-water emulsion that contains the desired drug in the oil.

* * * * *